United States Patent
Klimovitch et al.

(10) Patent No.: US 9,833,626 B2
(45) Date of Patent: *Dec. 5, 2017

(54) SYSTEMS AND METHODS FOR IMPLANTABLE MEDICAL DEVICE COMMUNICATION

(71) Applicant: Pacesetter, Inc., Sunnyvale, CA (US)

(72) Inventors: Gleb Klimovitch, Santa Clara, CA (US); Timothy Edward Ciciarelli, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,829

(22) Filed: Nov. 28, 2016

(65) Prior Publication Data

US 2017/0072205 A1   Mar. 16, 2017

Related U.S. Application Data

(62) Division of application No. 14/634,064, filed on Feb. 27, 2015, now Pat. No. 9,533,163.

(51) Int. Cl.
*A61N 1/372* (2006.01)
*A61N 1/375* (2006.01)
*A61N 1/39* (2006.01)
*A61N 1/362* (2006.01)

(52) U.S. Cl.
CPC ......... *A61N 1/37217* (2013.01); *A61N 1/362* (2013.01); *A61N 1/3756* (2013.01); *A61N 1/37205* (2013.01); *A61N 1/37229* (2013.01); *A61N 1/37252* (2013.01); *A61N 1/37276* (2013.01); *A61N 1/3956* (2013.01); *A61N 1/3968* (2013.01)

(58) Field of Classification Search
CPC ............ A61N 1/37217; A61N 1/37223; A61N 1/37229; A61N 1/37252; A61N 1/37276; A61N 1/37288; A61N 1/375; A61N 1/3756; A61N 1/36182; A61N 1/36185
See application file for complete search history.

(56) References Cited

U.S. PATENT DOCUMENTS

| | | | |
|---|---|---|---|
| 3,331,651 A * | 7/1967 | Sterzer | G02F 1/292 |
| | | | 359/298 |
| 4,760,852 A | 8/1988 | Lekholm | |
| 5,480,416 A | 1/1996 | Garcia | |
| 2008/0004670 A1 | 1/2008 | McVenes | |
| 2010/0305675 A1 | 12/2010 | Laske | |

(Continued)

OTHER PUBLICATIONS

Notice of Allowance dated Nov. 22, 2016; Related U.S. Appl. No. 14/634,064.

(Continued)

*Primary Examiner* — Eugene T Wu
(74) *Attorney, Agent, or Firm* — Theresa A. Raymer

(57) ABSTRACT

An implantable medical device (IMD) is configured to be implanted within a patient. The IMD may include a controller configured to adjust a communication frequency, a housing formed of an electrically common material, and an insulating cover coupled to the housing. The insulating cover may include one or both of at least one opening or at least one thinned area over portions of the housing. Multiple sub-electrodes are formed in the housing through the opening(s) or the thinned area(s).

16 Claims, 10 Drawing Sheets

(56) References Cited

U.S. PATENT DOCUMENTS

2012/0197349 A1    8/2012   Griswold
2012/0197350 A1    8/2012   Roberts

OTHER PUBLICATIONS

Amendment filed Nov. 3, 2016; Related U.S. Appl. No. 14/634,064.
Final Office Action dated Sep. 9, 2016; Related U.S. Appl. No. 14/634,064.
Amendment filed Aug. 1, 2016; Related U.S. Appl. No. 14/634,064.
Non-Final Office Action dated Mar. 31, 2016; Related U.S. Appl. No. 14/634,064.

* cited by examiner

SYSTEMS AND METHODS FOR IMPLANTABLE MEDICAL DEVICE COMMUNICATION

PRIORITY CLAIM

This application is a Divisional application of U.S. patent application Ser. No. 14/634,064, filed Feb. 27, 2015, entitled "SYSTEMS AND METHODS FOR IMPLANTABLE MEDICAL DEVICE COMMUNICATION," now U.S. Pat. No. 9,533,163, and is incorporated herein by reference in its entirety to provide continuity of disclosure.

BACKGROUND

Embodiments of the present disclosure generally relate to implantable medical devices, and, more particularly, to systems and methods for communicating between an implantable medical device and a remote programmer and/or another implantable medical device.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more electrodes that either receive or deliver voltage, current or other electromagnetic pulses (generally "energy") from or to an organ or tissue for diagnostic or therapeutic purposes.

An IMD communicates with a programmer and/or another IMD through a conductive communication channel, which is generally subject to gain nulls or fades when the IMD is at certain positions and/or orientations in relation to the other component with which it is communicating. The nulls or fades may prevent or otherwise reduce a communication capability of the IMD. In order to provide continuous communication, some known IMDs provide multiple communication sub-channels that include multiple electrodes having multiple driving wires therebetween. When the IMD is positioned at a particular orientation that would otherwise cause a communication null or fade, a different communication sub-channel may be used that is not subject to the communication null or fade.

Notably, the driving wires typically extend through implant walls, which may increase the cost of the IMD, due to additional sealing and connection interfaces. Additionally, the IMDs may also include multichannel transmit and/or receive hardware to accommodate multiple communication channels. Again, however, the addition of hardware adds cost and complexity to the IMDs.

Accordingly, a need exists for an efficient, cost-effective system and method of IMD communication.

SUMMARY

Certain embodiments of the present disclosure provide an implantable medical device (IMD) that is configured to be implanted within a patient. The IMD may include a controller configured to adjust a communication frequency, a housing formed of an electrically common material, and an insulating cover coupled to the housing. The insulating cover may include one or both of at least one opening or at least one thinned area over portions of the housing. Multiple sub-electrodes are formed on the housing through the opening(s) or the thinned area(s).

The housing may represent a physical electrode. The controller controls delivery of a communications signal to the physical electrode of the housing. The communication signal propagates from the multiple sub-electrodes along corresponding communications vectors that collectively define a composite transmit communications vector. In at least one embodiment, the controller selects a transmit frequency range of the communications signal to steer the composite transmit communications vector.

The insulating cover may have different first and second thicknesses in a first thinned area and outside of the first thinned area. The insulating cover may be configured to yield controlled capacitances that may be a function of thicknesses, areas, shapes, and locations of segments of the insulating cover on the housing.

The multiple sub-electrodes are configured to transmit and receive communication signals at different spatial orientations and different relative phase shifts. In at least one embodiment, the multiple sub-electrodes are configured to form multiple communication vectors that differ from one another. The multiple communication vectors may be formed due to complex impedances between different sub-electrodes having different phase angles at the same and/or different communication frequencies.

The housing may provide a single electrode that includes the multiple sub-electrodes. In at least one embodiment, the housing forms the single electrode. The IMD may also include a tip electrode coupled to the housing. The IMD may be, for example, an implantable pacemaker, an implantable cardioverter-defibrillator ("ICD"), a defibrillator, a cardiac rhythm management ("CRM") device, a neurostimulator, or the like.

Certain embodiments of the present disclosure provide a method of communicating with an implantable medical device (IMD). The method may include forming a plurality of sub-electrodes on the IMD through an insulating cover or an absence thereof, adjusting a communication frequency of the IMD with a controller, and/or changing a communication vector of the IMD through interaction of the adjusting and physical properties of the insulating cover.

The forming may include layering different thicknesses of insulating material onto a housing of the IMD. The method may also include controlling capacitances of the insulating cover. The capacitances may be a function of thicknesses, shapes, areas, and locations of segments of the insulating cover on the housing.

The method may include transmitting and receiving communication signals through the plurality of sub-electrodes at different spatial orientations and different relative phase shifts. The method may include forming multiple communication vectors that differ from one another. The multiple communication vectors may be formed by different interaction of spatially different sub-electrodes with tissue at the same or different communication frequencies.

Certain embodiments of the present disclosure provide a system for communicating with an implantable medical device (IMD) implanted within a patient. The system may include an external programmer, and at least one IMD configured to communicate with the external programmer.

DETAILED DESCRIPTION

Figure 1:
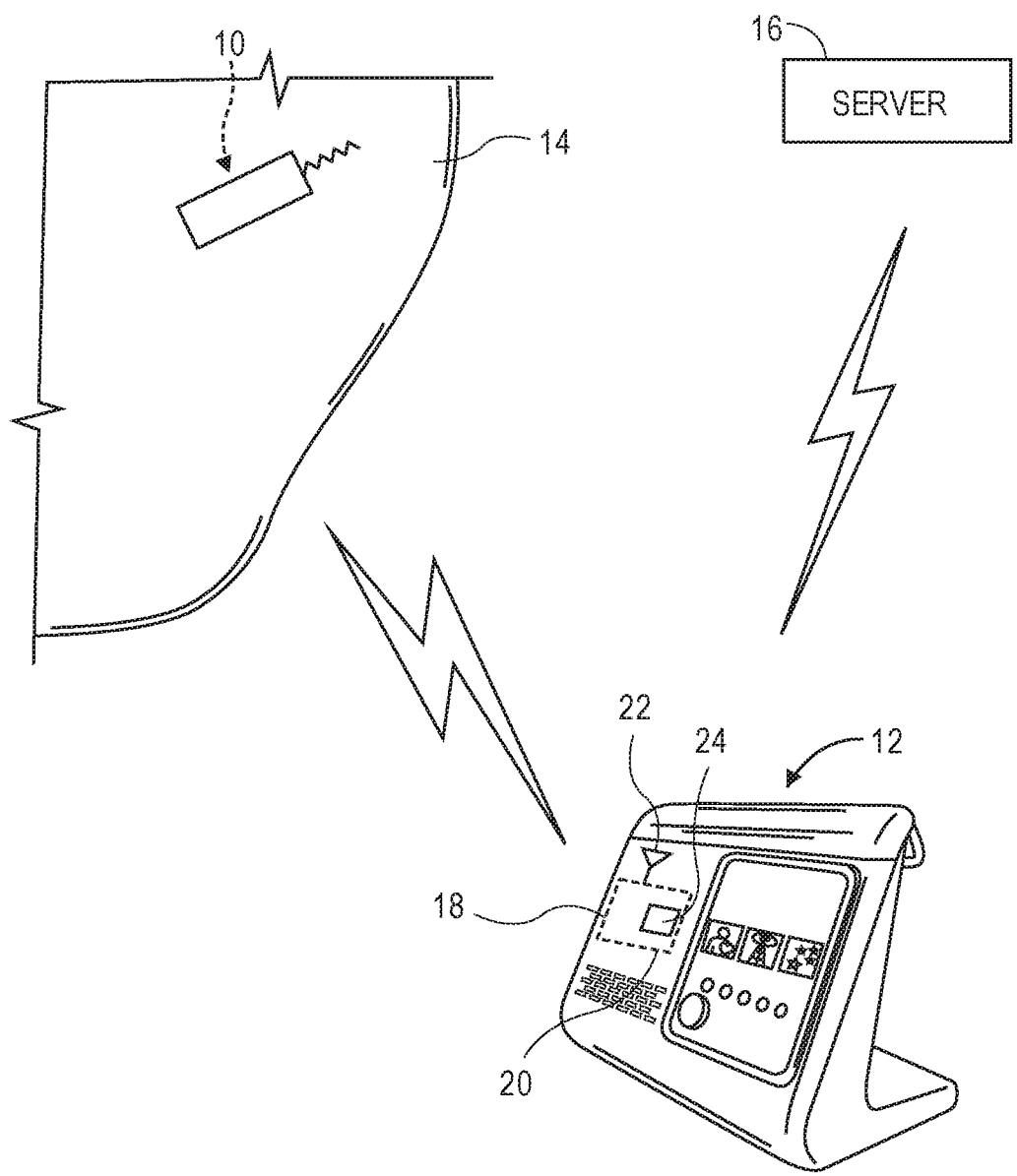
FIG. 1 illustrates a simplified view of an IMD and an external programmer, according to an embodiment of the present disclosure.

Embodiments of the present disclosure provide an IMD that may have multiple effective communication sub-channels. The communication sub-channels may exceed a number of physical sub-channels contained within circuitry of the IMD. The IMD may achieve multichannel performance and directional diversity during signal transmission and reception with single channel hardware inside the IMD, without the use of extra conductors. For example, an outer surface of the IMD may have areas that may be partially coated with insulating film(s) of controlled thickness and dielectric constant, thereby providing effective capacitor(s) between a housing and tissue of an individual.

Embodiments of the present disclosure provide an IMD that may effectively split or segment a single surface electrode into two or more parts (sub-electrodes) that may transmit and receive signals at different spatial orientations, and at different relative phase shifts. Because of the phase shift difference between the sub-electrodes of different spatial orientations, spatial diversity among sub-electrodes is preserved even when each sub-electrode is driven by a single transmit output channel and/or sensed by a single receive input channel. For example, transmitted currents from different sub-electrodes may differ in phase for the same driving voltage. At a low receive input impedance, receive partial inputs from different sub-electrodes differ in phase even when potentials received by outer surfaces of coated sub-electrodes are in phase.

The housing of the IMD may be coated with an insulation material, such as a dielectric. Different areas of the housing may be coated, non-coated, or coated at different depths. The insulating coating may provide capacitive layers of controlled capacitance per unit area.

Certain embodiments of the present disclosure provide an IMD that may be configured to communicate with an external programmer and/or other IMDs. A controller of the IMD and/or the external programmer may be configured to adjust transmit and receive frequencies of the IMD. The IMD may include a housing (such as a can, case, or the like) that is electrically common. For example, the housing may be a single piece of metal, which provides a unitary electrode. Portions of the IMD may be covered by an insulating cover, which may be or include a dielectric material. The insulating cover defines a plurality of sub-electrodes on the housing. For example, the insulating cover segments the single electrode of the housing into multiple sub-electrodes. At least portions of the insulating cover on the housing affect transmission of communication signals with respect to the location of the insulating cover on the housing. The insulating cover may have different thicknesses at different areas, with thickened areas completely or mostly blocking communication signals, and thinner areas partially blocking, phase shifting, or attenuating signals or allowing transmission and reception of the communication signals. The sub-electrodes may exhibit, generate, or introduce a sub-component of a communication vector (such as a transmit vector or receive vector) based on the thickness of the insulating cover. A combination of the sub-components may form a composite communication vector. The controller or external programmer may adjust a communication frequency (such as a transmit frequency or a receive frequency) to steer the composite communication vector.

The IMD may be any one of various types of implantable devices, such as, for example, an implantable pacemaker, implantable cardioverter-defibrillator ("ICD"), defibrillator, cardiac rhythm management ("CRM") device, neurostimulator, or the like. In at least one embodiment, the IMD may include a leadless cardiac pacemaker that may be enclosed in a hermetic housing (such as a can, case, or the like) that may be positioned on the inside or outside of a cardiac chamber. The pacemaker may have two or more electrodes located within, on, or near the housing, for delivering pacing pulses to muscle of the cardiac chamber and optionally for sensing electrical activity from the muscle, and for bidirectional communication with at least one other device within or outside the body. The housing may contain a primary battery to provide power for pacing, sensing, and communication, for example bidirectional communication. The housing may optionally contain circuits for sensing cardiac activity from the electrodes. The housing may contain circuits for receiving information from at least one other device via the electrodes and may contain circuits for generating pacing pulses for delivery via the electrodes. The housing may optionally contain circuits for transmitting information to at least one other device via the electrodes and may optionally contain circuits for monitoring device health. The housing may contain circuits for controlling these operations in a predetermined manner.

FIG. 1 illustrates a simplified view of an IMD 10 and an external programmer 12, such as a base station or patient care system (PCS), according to an embodiment of the present disclosure. The IMD 10 may be implanted within an individual 14. The remotely-located programmer 12 monitors the IMD 10. The programmer 12 may be located within a medical care facility, such as a hospital or clinic, or within a home of the individual 14, in his/her vehicle, at his/her office, and the like. When the programmer 12 is located within the individual's home, the programmer 12 may be proximate to a bed of the individual 14. The programmer 12 functions as a base station that wirelessly communicates with the IMD 10. The programmer 12 may also communicate with a remote server 16 within a patient care network, such as over a phone link, cellular link, Internet connection, local area network, wide area network and the like.

The programmer 12 performs various functions, such as operating as an intermediate relay device to collect and store patient physiologic data, IMD operational status data, and the like. The physiologic data may be electrical data related to a physiologic condition. The programmer 12 may then transmit the physiologic data, IMD operational status data and other data to the remote server 16 of the patient care network. Physicians and other personnel can monitor the patient and collect data over the patient care network. Also, the programmer 12 may receive updates, upgrades, and other IMD control-related information from the patient care network and relay the IMD control-related information to the IMD 10.

The programmer 12 may include a standalone antenna assembly. The programmer 12 may represent the Merlin® home patient care system offered by St. Jude Medical. The programmer 12 may include an RF telemetry subsystem 18 that communicates with the IMD 10 and/or the server 16. The telemetry subsystem 18 may include an RF telemetry circuit 20 operatively connected to one or more antennas 22. The telemetry circuit 20 may also include or be operatively connected to a controller, processing unit or circuit 24. Alternatively, the programmer 12 may represent a handheld portable tablet-type programmer device used by physicians and others to communicate with, collect data from, program, and reprogram the IMD 10. Also, alternatively, the programmer 12 may be a cell phone, personal computer, or laptop computer.

In operation, an RF chip within the IMD 10 may periodically scan a first frequency band. For example, the first frequency band may be an unlicensed, microwave band, such as a 2.45 GHz band. The IMD 10 may use information received over the first frequency band to determine if the programmer 12 is seeking to communicate with the IMD 10 over a second frequency band or channel, such as a higher power, lower frequency band, which may be used to receive and transmit data to and from the IMD 10. If the RF chip within the IMD 10 operating at the first frequency band detects that the programmer 12 desires to communicate over the second frequency band, the IMD 10 may switch over to the second frequency band.

A wand (not shown) may also be used to establish a communication link between the IMD 10 and the programmer 12. The wand may include an RF transmitter that transmits an RF wake-up call to the IMD 10 when in close proximity to the IMD 10. For example, the wand may be positioned within 0-1 meters from the IMD 10 in order to wake the IMD 10 up so that a communication link between the IMD 10 and the programmer 12 may be established. Alternatively, the wand may be able to wake the IMD 10 up at ranges longer than 1 meter. Once the wand transmits an RF wake signal to the IMD 10, the IMD 10 may then switch from the first frequency band to the second frequency band in order to communicate with the programmer 12. Also, the wand may be configured to be removably connected to a handheld device, such as an iPhone, iPad, Kindle, and/or the like.

Figure 2:
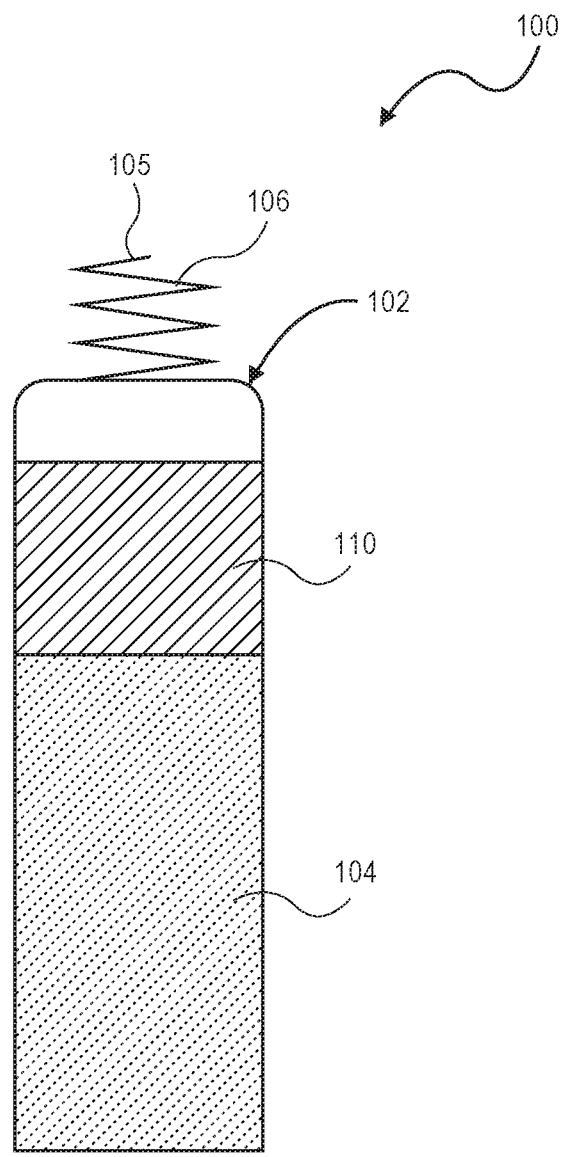
FIG. 2 illustrates a front view of an IMD, according to an embodiment of the present disclosure.

FIG. 2 illustrates a front view of an IMD 100, according to an embodiment of the present disclosure. The IMD 100 may include a hermetic housing 102 and electrodes 104 and 106 disposed thereon. For example, the housing 102 itself may provide a single electrode 104. In at least one embodiment, the metal shell of the housing 102 provides the electrode 104. In at least one other embodiment, a separate and distinct electrode 104 may be affixed to the housing 102. As described below, an insulating cover may be formed over the housing 102 and may define a plurality of sub-electrodes of the electrode 104. For example, the insulating cover may segment the electrode 104 into a plurality of sub-electrodes, which are segments, sub-parts, or other such portions of the electrode 104.

The electrode 106 may be a tip electrode and may also serve as a fixation mechanism 105. Optionally, the electrode 106 may be separated from but surrounded partially by the fixation mechanism 105. The fixation mechanism 105 may be or include a fixation helix, a plurality of hooks, barbs, or other attaching features configured to attach the IMD 100 to tissue, such as heart tissue.

The housing 102 may also include an electronics compartment 110 therein that contains the electronic components configured to operate the IMD 100, including, for example, a pulse generator, communication electronics, a battery, and one or more processors, such as a controller. The housing 102 may be configured to be implanted on or in a human heart, and may be cylindrically shaped, rectangular, spherical, or any other appropriate shapes, for example.

The housing 102 may be formed of a conductive, biocompatible, inert, and anodically safe material such as titanium, 316L stainless steel, or other similar materials. As noted, an insulating cover may be disposed over the housing 102 and define one or more sub-electrodes. The insulating cover may be or include an insulative coating on a portion of the housing between the electrodes 104 and 106, and may include a dielectric material, such as silicone, polyurethane, parylene, or another biocompatible electrical insulator commonly used for implantable medical devices. A single insulating cover may be layered, deposited, or otherwise disposed on the housing 102. The insulating cover may include areas having different thicknesses. Also, openings may be formed through the insulating cover. The openings expose an outer surface of the housing 102.

The electrodes 104 and 106 may include pace/sense electrodes, or return electrodes. A low-polarization coating may be applied to the electrodes, such as sintered platinum, platinum-iridium, iridium, iridium-oxide, titanium-nitride, carbon, or other materials commonly used to reduce polarization effects, for example. The electrode 106 may be a pace/sense electrode and the electrode 104 can be a return electrode.

Several techniques and structures may be used to attach the housing 102 to the interior or exterior wall of anatomy, such as the heart. The fixation mechanism 105 may be formed as a helical structure that may be used to insert the IMD 100 endocardially or epicardially through a guiding catheter. A torqueable catheter may be used to rotate the housing 102 and force the fixation mechanism 105 into tissue, thereby affixing the fixation mechanism 105 (and also the electrode 106) into contact with stimulable tissue. The electrode 104 may serve as an indifferent electrode for sensing and pacing. The fixation mechanism 105 may be coated partially or in full for electrical insulation, and a steroid-eluting matrix may be included on or near the IMD 100 to minimize fibrotic reaction, as is known in conventional pacing electrode-leads.

Figure 3:
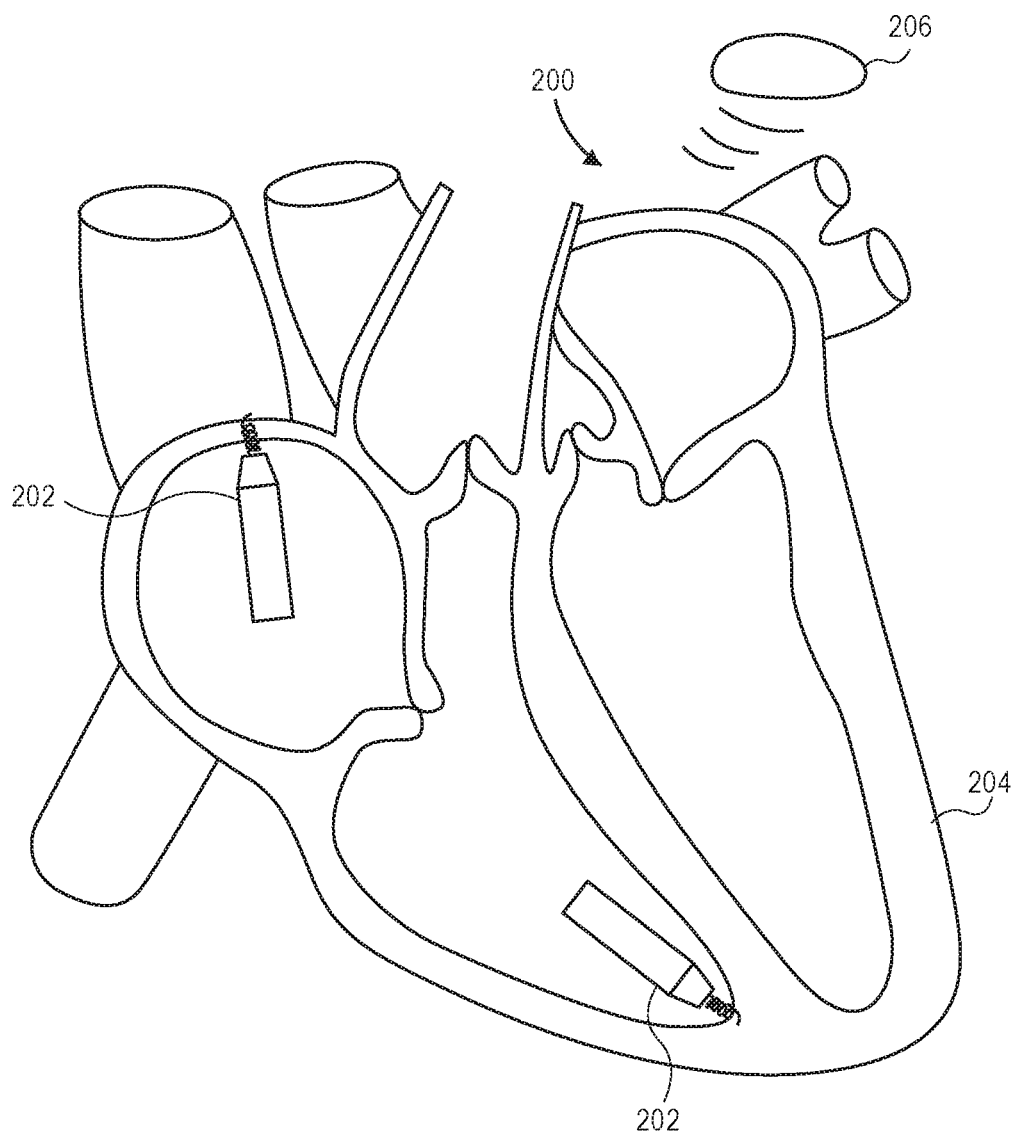
FIG. 3 illustrates a simplified internal view of a heart having implanted IMDs, according to an embodiment of the present disclosure.

FIG. 3 illustrates a simplified internal view of a heart 200 having implanted IMDs 202, according to an embodiment of the present disclosure. As shown, the IMDs 202 may be within the heart 200. Alternatively, the IMDs 202 may be implanted on an outer surface of the heart 200. Also, alternatively, the IMDs 202 may be implanted on or within various other anatomical structures, such as a brain, lung, or the like.

As shown in FIG. 3, the IMDs 202 may be configured to perform cardiac pacing in conjunction with an implantable cardioverter-defibrillator (ICD) 206. The IMDs 202 may be configured to implement, for example, single-chamber pacing, dual-chamber pacing, or three-chamber pacing for cardiac resynchronization therapy, without requiring pacing lead connections to the ICD 206. The IMDs 202 may be in electrical contact with a cardiac chamber 204 and configured to perform cardiac pacing functions in combination with the ICD 206.

The IMDs 202 may communicate with one another, a non-implanted programmer (such as the programmer 12 shown in FIG. 1), and/or the implanted ICD 206 via the same electrodes that are also used to deliver pacing pulses. The IMDs 202 may be configured to communicate via communication that has outgoing communication power requirements that may be met by power consumed in cardiac pacing.

In some embodiments, the individual IMDs 202 may include a hermetic housing configured for placement on or attachment to the inside or outside of a cardiac chamber 204 and at least two leadless electrodes proximal to the housing and configured for bidirectional communication with at least one other device 206 within or outside the body. The IMDs 202 may be pacemakers having at least two electrodes located within, on, or near respective housings for delivering pacing pulses to and sensing electrical activity from the muscle of the cardiac chamber, and for bidirectional communication with at least one other device within or outside the body.

While FIG. 3 shows two IMDs 202, it is to be understood that more or less IMDs 202 may be used. For example, only a single IMD 202 may be implanted in or on the heart 200. The single IMD 202 may communicate with the ICD 206 and/or an external programmer. Also, the ICD 206 may not be used. Instead, one or more ICDs 206 may communicate with a remote programmer.

Figure 4:
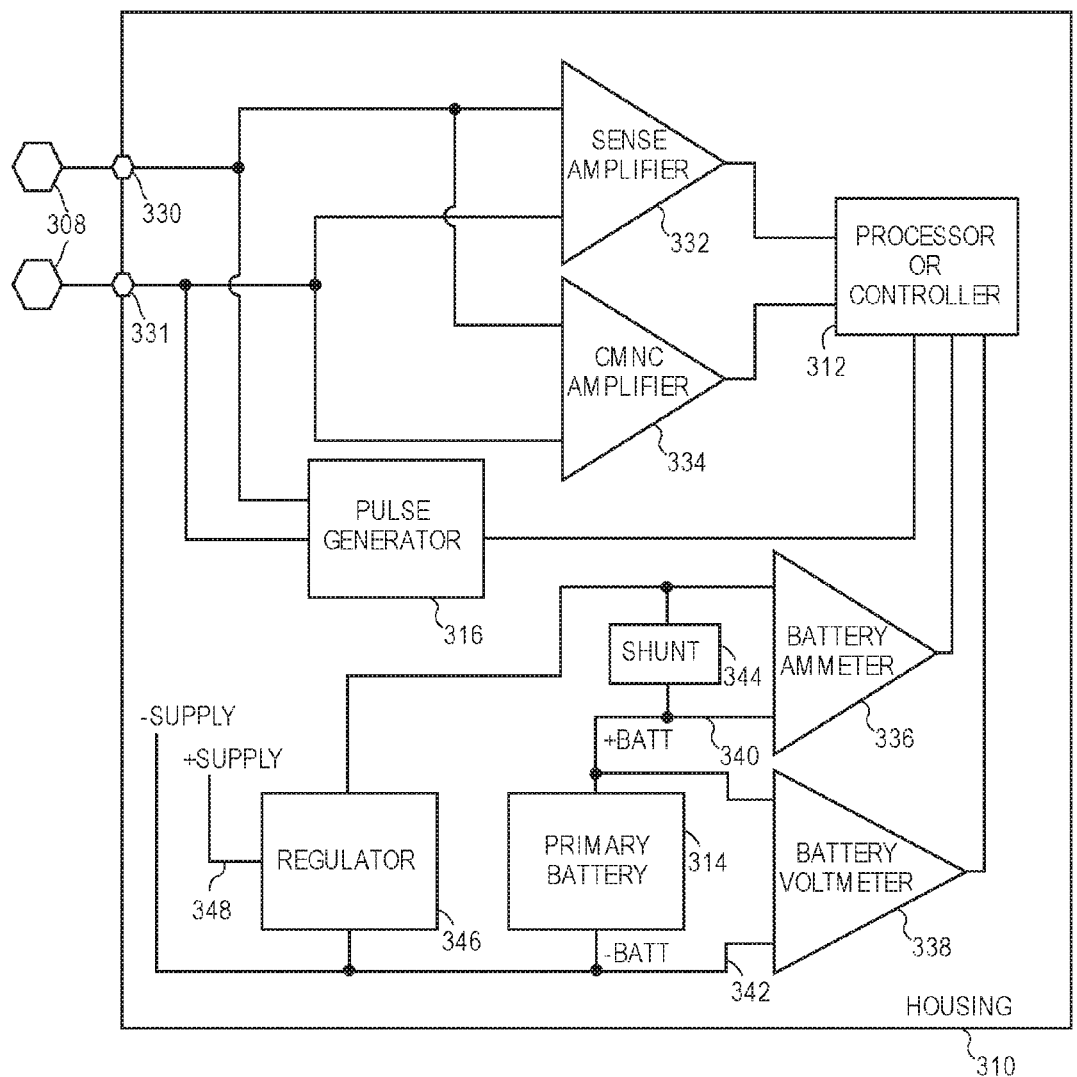
FIG. 4 illustrates a schematic block diagram of an IMD, according to an embodiment of the present disclosure.

FIG. 4 illustrates a schematic block diagram of an IMD 300, according to an embodiment of the present disclosure. The IMD 300 may include at least two electrodes 308 located within, on, or near a housing 310, for delivering pacing pulses to and sensing electrical activity from the muscle of the cardiac chamber, and for bidirectional communication with at least one other device within or outside the body. Hermetic feedthroughs 330, 331 conduct electrode signals through the housing 310. Optionally, the IMD 300 may include only one feedthrough, such as if the housing 310 itself is or provides one of the electrodes. The housing 310 contains a primary battery 314 to supply power for pacing, sensing, and communication. The housing 310 also contains circuits 332 for sensing cardiac activity from the electrodes 308, circuits 334 for receiving information from at least one other device via the electrodes 308, and a pulse generator 316 for generating pacing pulses for delivery via the electrodes 308 and also for transmitting information to at least one other device via the electrodes 308. The housing 310 may also contain circuits for monitoring device health, such as, for example, a battery current monitor 336 and a battery voltage monitor 338, and circuits for controlling operations in a predetermined manner.

The electrodes 308 may be configured to communicate bi-directionally among other IMDs, an implanted device (such as an implanted ICD), and/or a programmer to coordinate therapy delivery using messages that identify an event at an individual IMD originating the message and another IMD receiving the message as directed by the message depending on the origin of the message. An IMD that receives the message reacts as directed by the message depending on the message origin or location. In some embodiments or conditions, the two or more electrodes 308 may be configured to communicate bi-directionally and transmit data including designated codes for events detected or created by an individual IMD. Individual IMDs may be configured to issue a unique code corresponding to an event type and a location of the sending IMD.

Information communicated on the incoming communication channel may include but is not limited to pacing rate, pulse duration, sensing threshold, and other parameters commonly programmed externally in conventional pacemakers. Information communicated on the outgoing communication channel may include but is not limited to programmable parameter settings, pacing and sensing event counts, battery voltage, battery current, device health, and other information commonly displayed by external programmers used with conventional pacemakers. The outgoing communication channel may also echo information from the incoming channel, to confirm correct programming.

The primary battery 314 may include a positive terminal 340 and negative terminal 342. Current from the positive terminal 340 flows through a shunt 344 to a regulator circuit 346 to create a positive voltage supply 348 suitable for powering the remaining circuitry of the IMD 300. The shunt 344 allows the battery current monitor 336 to provide the processor or controller 312 with an indication of battery current drain and indirectly of device health.

Figure 5:
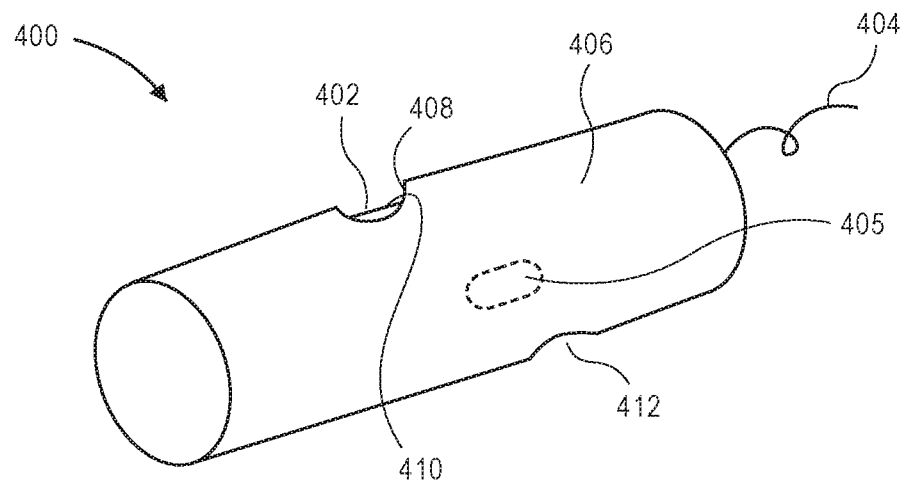
FIG. 5 illustrates a perspective view of an IMD, according to an embodiment of the present disclosure.

FIG. 5 illustrates a perspective view of an IMD 400, according to an embodiment of the present disclosure. The IMD 400 includes a housing 402 and a tip electrode 404. The housing 402 may retain a controller 405 that is configured to adjust a communication frequency of the IMD 400. Optionally, an external programmer may adjust a communication frequency of the IMD 400. For example, the IMD 400 may transmit or receive signals over the various different communication frequencies (for example, at a first frequency when communicating with an external device and at a second frequency when communicating with another IMD). The housing 402 may be an electrically common can or case that provides a single electrode. For example, the housing 402 itself may be an electrode. Optionally, a separate and distinct electrode may be secured to the housing 402.

An insulating cover 406 formed of a dielectric material covers portions of the housing 402. The insulating cover 406 may cover more or less areas of the housing 402 than shown. A thickness of the insulating cover 406 may be different at different portions. For example, an opening 408 may be formed through the insulating cover 406 exposing an outer surface 410 of the housing 402. The exposed outer surface 410 provides a sub-electrode of the housing 402 (which may provide a single, unitary electrode). Signals (for example, therapeutic energy and communication signals) may be transmitted and received through the sub-electrode, as defined by the exposed outer surface 410. The covered portions of the housing 402 may be completely or partially blocked from transmitting or receiving signals by the insulating cover 406.

The insulating cover 406 may also include thinned areas 412 at certain areas over the housing 402. The thinned areas 412 may be divots, depressions, sunken areas, compressed areas, or the like formed in the insulating cover 406. The thinned areas 412 may have a thickness that is less than a thickness of the insulating cover 406 in non-thinned areas. The select thickness of the thinned areas 412 is sufficiently thin to allow communications signals to pass through the thinned areas 412. For example, a first thinned area 412 forms a dielectric layer for a corresponding covered area of the housing 402 to define a first sub-electrode at the thinned area 412. Additionally or alternatively, second, third, etc.

thinned areas may form dielectric layers for corresponding covered areas of the housing 402 to define second, third, etc. sub-electrodes. Each sub-electrode has a location, size and shape matching the location, size and shape of the corresponding thinned area 412. The thickness of the dielectric material (insulating cover) in the thinned area 412, in part, defines the electrical properties of the sub-electrode. For example, when transmitting a communications signal at a select frequency, the sub-electrode exhibits select impedance and introduces a corresponding phase shift into the transmitted communications signal. Similarly, when receiving a communications signal at a select frequency, the sub-electrode exhibits a select impedance and introduces a corresponding phase shift into the received communications signal. For a given dielectric thickness, as the transmit and/or receive frequency is varied, the phase shift introduced by the sub-electrode into the transmit/receive signal varies.

As a further example, when first and second thinned areas have different dielectric thicknesses, the corresponding first and second sub-electrodes exhibit different first and second impedances, respectively. For a given transmit frequency, the first and second sub-electrodes introduce first and second phase shifts, respectively, into the transmitted communications signal. For a given receive frequency, the first and second sub-electrodes introduce first and second phase shifts, respectively, into the received communications signal.

The sub-electrodes defined by thinned areas 412 cooperate to define a virtual electrode positioned at a select, but arbitrary location on the housing 402. The sub-electrodes defined by thinned areas 412 also cooperate to define an arbitrary, but select shape and size of the virtual electrode. The sub-electrodes (and thus the virtual electrode) and the electrode 404 cooperate to define a transmit vector associated with transmitting communications signals and to define a receive vector associated with receiving communications signals.

By changing a dielectric thickness of the insulating cover, the thinned areas 412 affect communication vectors of communication signals (transmit and receive) depending on a frequency of the communication signals, as described below.

In the embodiments described above in connection with FIG. 3, the thickness of the insulating cover in the thinned areas 412 attenuate or otherwise affect the transmit/receive properties of communication signals that pass therethrough. Additionally or alternatively, a conductive metal may be positioned in the thinned areas 412 to provide a modified sub-electrode that allows communication signals to pass therethrough while affecting transmit/receive properties of the communication signals in a select manner.

The IMD 400 may include more or less openings 408 and/or thinned areas 412 than shown. Further, the shapes and sizes of the openings 408 and the thinned areas 412 may be different than shown and different from one another. Each opening 408 may be circular, elliptical, rectangular, triangular, irregularly-shaped, or various other shapes. Similarly, the thinned areas 412 may be various shapes and sizes.

In operation, the sub-electrodes of the housing 402 provide defined areas of the housing 402 that are configured to transmit and receive signals. In this manner, the sub-electrodes of the single electrode (which may be defined by the housing 402 itself) are configured to transmit and receive signals in relation to communication vectors that vary as a function of the dielectric properties of the insulating cover 406 and as a function of a frequency of the communication signal. For example, the dielectric properties of the insulating cover 406 and the frequency of the communication signal may interact to steer a communication signal over a particular communication vector. In at least one embodiment, the IMD selectively switches between communication vectors by adjusting a communication frequency, which interacts with physical properties of the insulating cover to cause the communication vectors to change in response.

Figure 6:
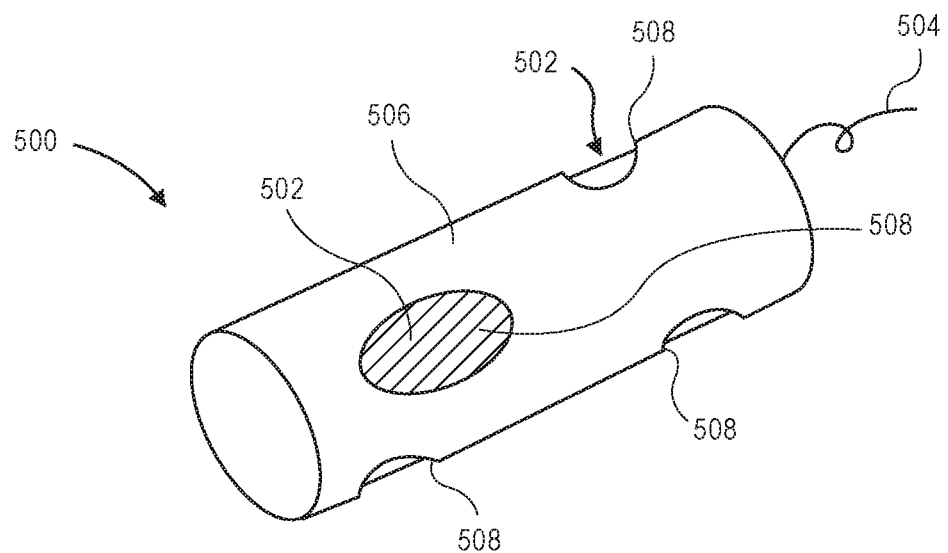
FIG. 6 illustrates a perspective view of an IMD, according to an embodiment of the present disclosure.

FIG. 6 illustrates a perspective view of an IMD 500, according to an embodiment of the present disclosure. The IMD 500 may include a housing 502, which serves as or otherwise provides a single electrode, and a separate and distinct tip electrode 504. An insulating cover 506 covers portions of the housing 502 and includes a plurality of openings 508 that define a corresponding number of sub-electrodes of the single electrode of the housing 502. The insulating cover 506 may also include one or more thinned areas, which may also define separate and distinct sub-electrodes. The IMD 500 may include more or less sub-electrodes than shown.

Figure 7:
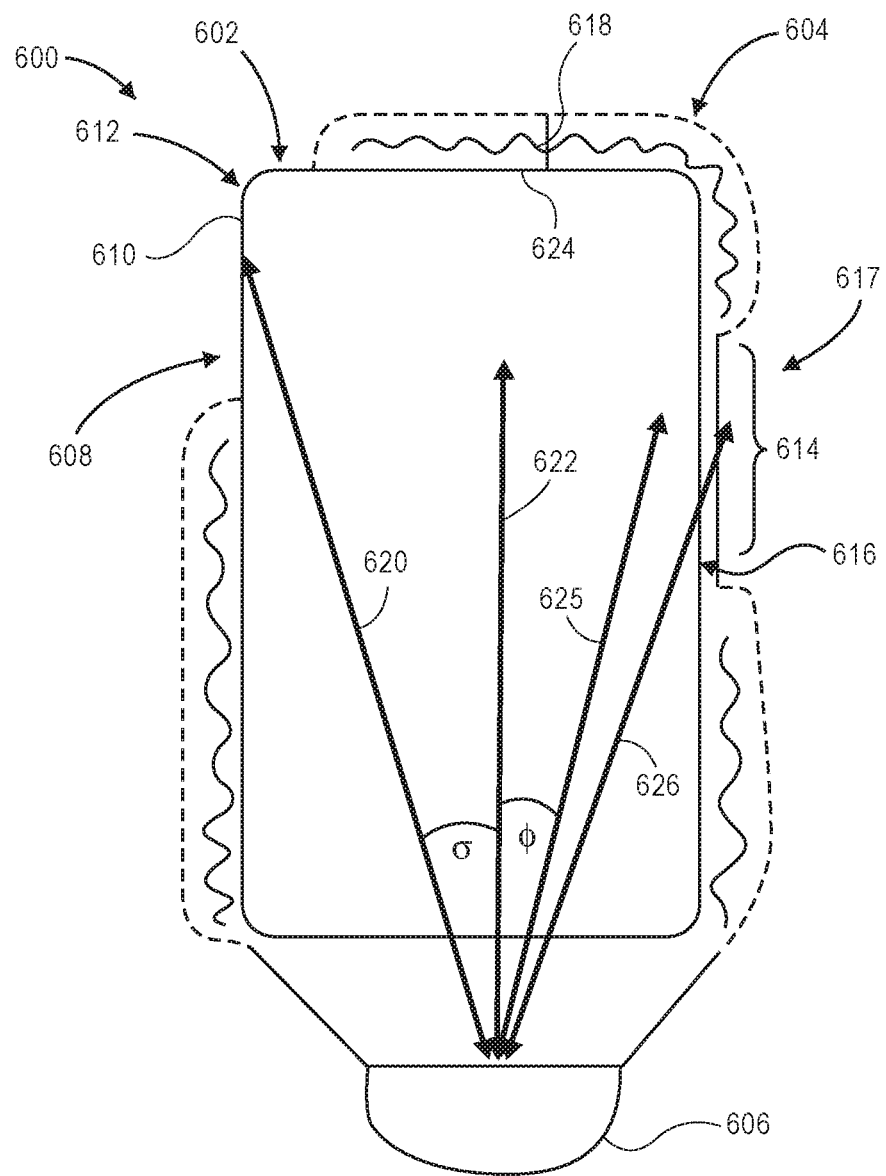
FIG. 7 illustrates a simplified transverse cross-sectional view of an IMD, according to an embodiment of the present disclosure.

FIG. 7 illustrates a simplified transverse cross-sectional view of an IMD 600, according to an embodiment of the present disclosure. The IMD 600 includes a housing 602, such as a can or case, that provides a single, electrically common structure that acts as a single electrode. A separate and distinct electrode 606, such as a tip electrode, may be connected to the housing 602. An insulating cover 604, formed of a dielectric material, covers outer portions of the housing 602. The insulating cover 604 may be a single covering structure having openings and thinned areas. Optionally, the insulating cover 604 may be or include multiple segments that are deposited on or otherwise secured to areas of the housing 602 separated by open areas (e.g., openings).

The housing 602 may be or otherwise represent a physical electrode. A controller controls delivery of a communications signal to the physical electrode of the housing 602. The communication signal propagates from multiple sub-electrodes along corresponding communications vectors that collectively define a composite transmit communications vector. In at least one embodiment, the controller selects a transmit frequency of the communications signal to steer the composite transmit communications vector. The insulating cover 604 may have different first and second thicknesses in a first thinned area and outside of the first thinned area.

As noted, an opening 608 may be formed through the insulating cover 604. The opening 608 exposes a portion 610 of an outer surface area of the housing 602. The exposed portion 610 provides a sub-electrode 612 of the single electrode defined by the housing 602.

A thinned area 614 may be formed in the insulating cover 604 at another area over the housing 602. The thinned area 614 may have a thickness 616 that is less than a thickness 618 of a main portion of the insulating cover 604. The thinned area 614 may provide a separate and distinct sub-electrode. The reduced area 614 affects a communication vector of a communication signal (such as one or more transmit or receive signals) of the IMD 600. The thickness 616 may be varied depending on a desired direction of the communication vector.

In operation, the IMD 600 may communicate with another component, such as another IMD, an external programmer, an ICD, or the like, via communication vectors. In at least one embodiment, changes in a frequency range of a communication signal may change a phase angle of sub-electrode impedance due to the insulating cover, thereby steering a communication vector to a desired direction. For example, even though the IMD 600 includes the single electrode of the housing 602 and the tip electrode 606, the IMD 600 may be selectively operated with respect to multiple communication vectors. The communication vectors may be a function of the insulating cover 604 and a frequency range of the communication signal.

In at least one embodiment, a first frequency (for example, a relatively low frequency), neither the thicker insulating cover 604, nor thinned insulation area 614 conduct, and a communication vector may coincide or almost coincide with vector 620 that extends through the sub-electrode 612. When the communication signal is changed to a second frequency that differs from the first frequency (or example, a significantly higher frequency), the thinned insulation area starts to capacitatively conduct, which steers the communication vector towards a communication vector 626 that extends through the thinned insulation area 614 so that the resulting communication vector 622 is a linear combination of vectors 620 and 626. At a third frequency that may be higher than the second frequency, a composite vector is still a linear combination of vectors 620 and 626, but with a larger contribution from vector 626 and a smaller contribution from vector 620, resulting in vector 625. Notably, the extension of communication vector 622 may pass through a thickened portion of the insulating cover 618 that is not a sub-electrode.

As one example, at a first frequency, a communication signal may be transmitted or received over the communication vector 620 in relation to the sub-electrode 612 and the electrode 606. For example, the communication vector 620 may be generated within a frequency range of 5-15 kHz. Alternatively, the frequency range may be greater or lesser than 5-15 kHz.

As the frequency of the communication signal is changed, the areas of different insulation thickness (e.g., the opening 608, the thickened areas of the insulating cover 604, and the thinned area 614) affect the communication vector. For example, at a frequency range between 50-250 kHz, the communication vector 622 (which may be a composite vector of the communication vectors 620 and 622) is generated between the electrode 606 and through a covered top portion 624 of the housing 602. As shown, the communication vector 622 may be steered or otherwise shifted an angle θ from the communication vector 620. At a different frequency range, such as over 500 kHz, the communication vector 625 (which is closer to the vector 626) may result. The communication vector 622 may be steered or shifted an angle φ from the communication vector 622.

Thus, at different communication frequencies, different communication vectors 620, 622, and 626 may result. The communication frequencies interact with the physical structure and location of the insulating cover 604 to generate the communication vectors 620, 622, and 626. In response to a signal being transmitted to or received at a first frequency, the communication vector 620 occurs. In response to a signal being transmitted or received at a second frequency (that differs from the first frequency), the communication vector 622 occurs. In response to a signal being transmitted or received at a third frequency (that differs from the first and second frequencies), the communication vector 626 occurs. More or less communication vectors may be used, depending on the number of openings, thinned areas, and various thicknesses of the insulating cover (which may be greater or lesser than shown).

The insulating cover 604 provides a dielectric coating that may be layered, deposited, or otherwise secured over one or more areas of the electrode (which may be or be provided by the housing 602). The insulating cover 604 yields controlled capacitances, which may be a function of a thickness and location of segments of the insulating cover 604. Different frequencies steer, shift, or otherwise change the physical communication vectors.

In at least one embodiment, the insulating cover 604, or another insulating cover, may cover portions of the tip electrode 606. As such, the tip electrode 606 may also be divided, segmented or partitioned into a plurality of sub-electrodes.

Each communication vector may be or include a dipole, which may include a positive and negative charge separated by a distance. For example, the electrode 606 may provide a positive charge and the sub-electrode 612 (separated by the distance from the sub-electrode 612 to the electrode 606) may provide a negative charge. When the communication signal is a transmit signal, the signal may be transmitted along the communication vector 620 in a direction from the electrode 606 to the sub-electrode 612.

Thus, embodiments of the present disclosure provide an IMD that includes a single housing covered by an insulating cover having varying thickness throughout. The IMD provides electrical diversity without the need for separate and distinct electrodes. Instead, the housing provides a single electrode with sub-electrodes defined through openings and/or thinned areas formed through the insulating cover.

The following analysis provides derivations and explanations that explain why the communication vectors may be steered as described above. A voltage V_RX at an electrode dipole vector d_RX in terms of the transmitting dipole vector d_TX is determined as follows:

$$V\_RX = I\_TX * rho * [(d\_RX * d\_TX) - 3*(d\_RX * n)(d\_TX * n)])/(4*pi*R^3),$$

where I_TX is the current through a transmitter dipole, rho is tissue resistivity, n is the unit vector along an implant-implant or dipole-dipole line, and R is the distance between TX and RX (electrode dipoles). d_TX and d_RX are spatial vectors connecting transmitting and receiving electrode pairs, respectively, so that the dimension of d_TX and d_RX is that of length.

Thus the channel gain is zero whenever d_RX is perpendicular to the electric field created by d_TX at the location of the receiver. For a given transmitter orientation (d_TX) and relative implant-implant placement (n), there is a one-dimensional submanifold (circle) out of a two-dimensional receiver orientation manifold (sphere of the directions of d_RX), for which channel gain is zero. Therefore, channel gain will be low (for example, zero) for such orientations of d_RX.

If the transmitter has two independent sub-channels with the corresponding dipole vectors d_TX1 and d_TX2, then simultaneous fading on both sub-channels occurs when both of the following voltages are zero:

$$V\_RX1 = I\_TX1 * rho * [(d\_RX * d\_TX1) - 3*(d\_RX * n)(d\_TX1 * n)])/(4*pi*R^3)$$

$$V\_RX2 = I\_TX2 * rho * [(d\_RX * d\_TX2) - 3*(d\_RX * n)(d\_TX2 * n)])/(4*pi*R^3)$$

In other words, both sub-channel gains are zero when d_RX is perpendicular to both electric fields created by d_TX1 and d_TX2 at the location of the receiver. Because there are two such orientations (for example, two opposite points rather than the whole circle on the sphere of d_RX orientations), this directional diversity at the transmitter strongly reduces the probability of fading. To further reduce or even remove fading, additional TX and/or RX sub-channels may be added.

It may not suffice to merely increase the number of electrodes, because driving d_TX1 and d_TX2 with the same TX voltage (V_TX1=V_TX2) may not result in directional diversity. Instead, it may result in I_TX1 and I_TX2 being in constant ratio and in phase, so that electric fields created by them at RX may combine into a field of constant direction. Therefore, it may suffice to orient d_RX perpendicular to this direction to get fading. Thus V_TX1=V_TX2 may be meaningless, as it may effectively reverse the system back to one-TX-sub-channel performance.

To preserve directional diversity without having two independent sub-channel drivers at TX, the IMD may use passive circuit elements in series between the single TX driver output and TX sub-electrodes, which may be on or near the outer surface of the IMD and do not require extra wiring through the housing.

Figure 8:
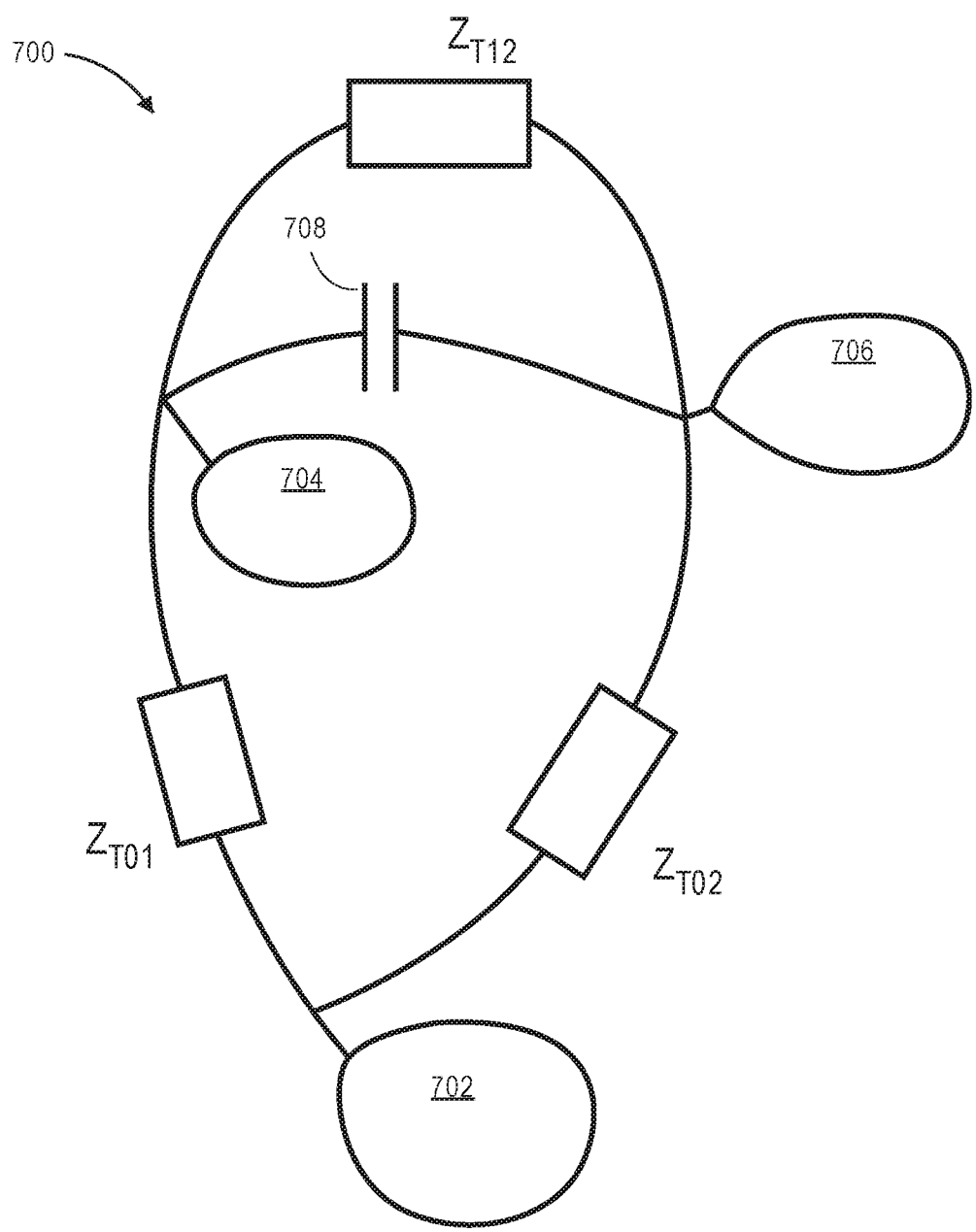
FIG. 8 illustrates a simplified schematic of an IMD circuit, according to an embodiment of the present disclosure.

FIG. 8 illustrates a simplified schematic of an IMD circuit 700, according to an embodiment of the present disclosure. As shown in FIG. 8, the same V_TX may be applied between the following sub-circuits: the tip electrode 702 and sub-electrode 704, and the tip electrode 702 and sub-electrode 706 in series with capacitor 708 of value C_12 formed by the thinned insulating coating between the can metal and the tissue. Z_T01, Z_T02, and Z_T12 represent the impedance (through tissue) between electrode pairs 702-704, 702-706, and 704-706, respectively. Let V_TX1=V_TX and V_TX2 be the voltages between electrodes 702-704 and 702-706, respectively. Then at angular frequency w, the frequency (Fourier) components Vw_TX1, Vw_TX2 of these voltages are as follows:

$$Vw\_TX2/Vw\_TX1 = (j*w*C\_12 + 1/Zw\_T12)/(j*w*C\_12 + 1/Zw\_T12 + 1/Zw\_T02)$$

$$Vw\_TX1/Vw\_TX2 = 1 + 1/(Zw\_T02*j*w*C\_12 + Zw\_T02/Zw\_T12)$$

where Zw_T01, Zw_T02, and Zw_T12 are frequency (Fourier) components of Z_T01, Z_T02, and Z_T12, respectively.

Therefore, Vw_TX1 and Vw_TX2 will generally be out of phase, and so will Iw_TX1 and Iw_TX2, which are the frequency components of the currents sourced by sub-electrodes 704 and 706, respectively (with the return path through electrode 702). If both the phase shift between TX currents Iw_TX1 and Iw_TX2 and the angle between d_TX1 and d_TX2 are significant (e.g. ¼ of radian or more), then directional diversity is achieved with a single TX channel and a single feedthrough wire to both sub-electrode 704 and sub-electrode 706 through capacitor 708.

One way to achieve a large phase shift between Iw_TX1 and Iw_TX2 is to have a small enough ratio (|Zw_T02|/|Zw_T12|) and by choosing certain operating frequencies.

$$beta = sqrt(|Zw\_02T/Zw\_12T| + |Zw\_02T/Zw\_12T|^2)$$

Assuming that Zw_T012, Zw_T02, and Zw_T12 are all in the communication frequency range, the phase shift between Iw_TX1 and Iw_TX2 is maximized at the following:

$$w\_MaxPhaseShift = 1/(|Zw\_02T|*sqrt(beta+beta^2))$$

which equals (in radians):

$$MaxPhaseShift = a\,tan\,[1/(2beta)]$$

For example, |Zw_T12|<|Zw_T02| results in beta<sqrt(2) and MaxPhaseShift>⅓ rad. Because a can surface area (e.g., the surface area of the housing) exceeds that of the tip surface area, the impedance between large uncoated parts of the can is less than the can-tip impedance. This may result in an impractically high ratio (|Zw_T02|/|Zw_T12|), unless a special coating strategy is used.

Referring again to FIG. 7, the thinned area 614 may provide a sub-electrode 617. The surface area of the sub-electrode 617 may be a first area, and surrounded on its sides by relatively thick coating (with negligible capacitance through the coating layer). The thick coating increases the distance the current between sub-electrode 612 and sub-electrode 617 has to travel, thereby increasing |Zw_T12|, to levels >=|Zw_T02|, for example.

The effective surface area of the sub-electrode 617 may also be reduced by thickly coating a significant part of the housing 602, which may equalize TX currents I_TX1 and I_TX2, as well as increase the angle between d_TX1 and d_TX2.

In FIG. 7, the equipotential outer surface of coated sub-electrode 617 is approximately equipotential, and, alternatively, may be made almost exactly equipotential. For example, the thin insulation of sub-electrode 617 may be coated with metal film on the surface of the thinned area 614 of the insulating cover 604. However, if blood wets the thinned area 617 so that the capacitance of a coating-blood boundary layer is large enough (e.g. larger than the capacitance of the thinned area 614 per the same surface area), the metal film may not be necessary. In other words, the sub-electrode 617 may provide a virtual electrode created by thinly coating part of the housing 604 with insulating material (such a dielectric material).

Instead of and/or in addition to generating spatial diversity at a transmit signal (TX), the same can be generated at a receive signal (RX). Obtaining such diversity without increasing the number of wires to the receiver may be achieved in a similar fashion as described above. For example, suppose that V_RX1 and V_RX2 are open circuit voltages received by d_RX1 and d_RX2, respectively (that is, voltages in the absence of currents I_RX1 and I_RX2 into sub-electrodes 612 and 617, which may correspond to sub-electrodes 704 and 706, as shown in FIG. 8). There will generally be nonzero RX currents I_RX1 and I_RX2. Significant phase shift between I_RX1 and I_RX2 may be achieved, even if V_RX1 and V_RX2 are in phase. For example, this occurs when |Zw_02| and |Zw_01| are of the same order of magnitude. |Zw_12| is larger than or comparable with |Zw_02| and |Zw_01|, the receiver input impedance |Zinw_12| is smaller than or comparable in magnitude with |Zw_02| and |Zw_01|, and angular frequency w is of the order of w~1/(C_12*|Zw_02|), i.e. under conditions overlapping with those for spatial diversity at the transmitter. The extra spatial diversity helps to further reduce channel fading.

Additionally, more than two sub-electrodes per one physical channel may be created, such as by properly coating the housing. For example, the corresponding dipole vectors may be non-planar, which also helps to overcome or mitigate channel fading.

Further, with frequency-dependent spatial diversity created through sub-electrodes at TX and/or RX, the residual fading also becomes frequency dependent. Therefore, by using either wide-band communication or narrow-band communication with more than one carrier frequency, residual fading may be eliminated, minimized, or otherwise reduced.

As described above, the electrode as defined as or part of the housing may be split into a plurality of sub-electrodes. Additionally, spatial diversity may also be increased by splitting a tip electrode, such as the electrode 606 shown in FIG. 7, into sub-electrodes by covering portions thereof with an insulating cover. For example, a metal patch may be formed on the surface of a thickly coated part of the housing, which is electrically connected to the tip electrode (such as by a metal trace running over the thick coat of the insulating cover). The trace may be insulated with thick insulating coating over it (for low trace-tissue capacitance). The metal patch may be thinly coated to create a desired value of capacitance. Optionally, another metal patch may be positioned over the thin coat on top of the existing metal patch. Thus the original tip electrode is expanded into a first tip sub-electrode and a second tip sub-electrode. Also, besides capacitors, surface resistors may be created on the housing and/or the tip electrode.

As described above, embodiments of the present disclosure provide an IMD that is configured to communicate with another IMD, a programmer, and/or another component with minimal or otherwise reduced channel fading. Spatial diversity is achieved without the need for extra hardware inside the IMD or running extra wires through a housing of the IMD.

Figure 9:
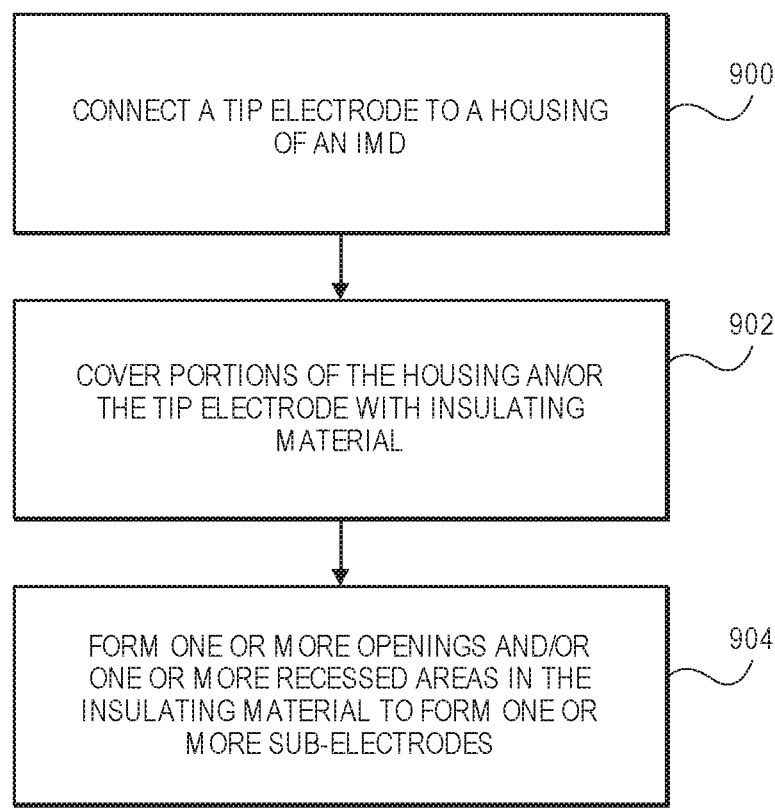
FIG. 9 illustrates a flow chart of a method of forming an IMD, according to an embodiment of the present disclosure.

FIG. 9 illustrates a flow chart of a method of forming an IMD, according to an embodiment of the present disclosure. At 900, a tip electrode may be connected or coupled to a housing of an IMD. The housing may be or include a can electrode, for example. Next, at 902, portions of the housing and/or the tip electrode are covered with insulating material. For example, insulating material, in the form of a dielectric material, may be layered, deposited, adhesively applied, or otherwise secured to outer portions of the housing and/or the tip electrode. At 904, one or more openings and/or thinned areas are formed through the insulating material to form one or more sub-electrodes. For example, the single electrode of the housing may be divided into multiple sub-electrodes through openings and/or thinned areas of the insulating material.

Figure 10:
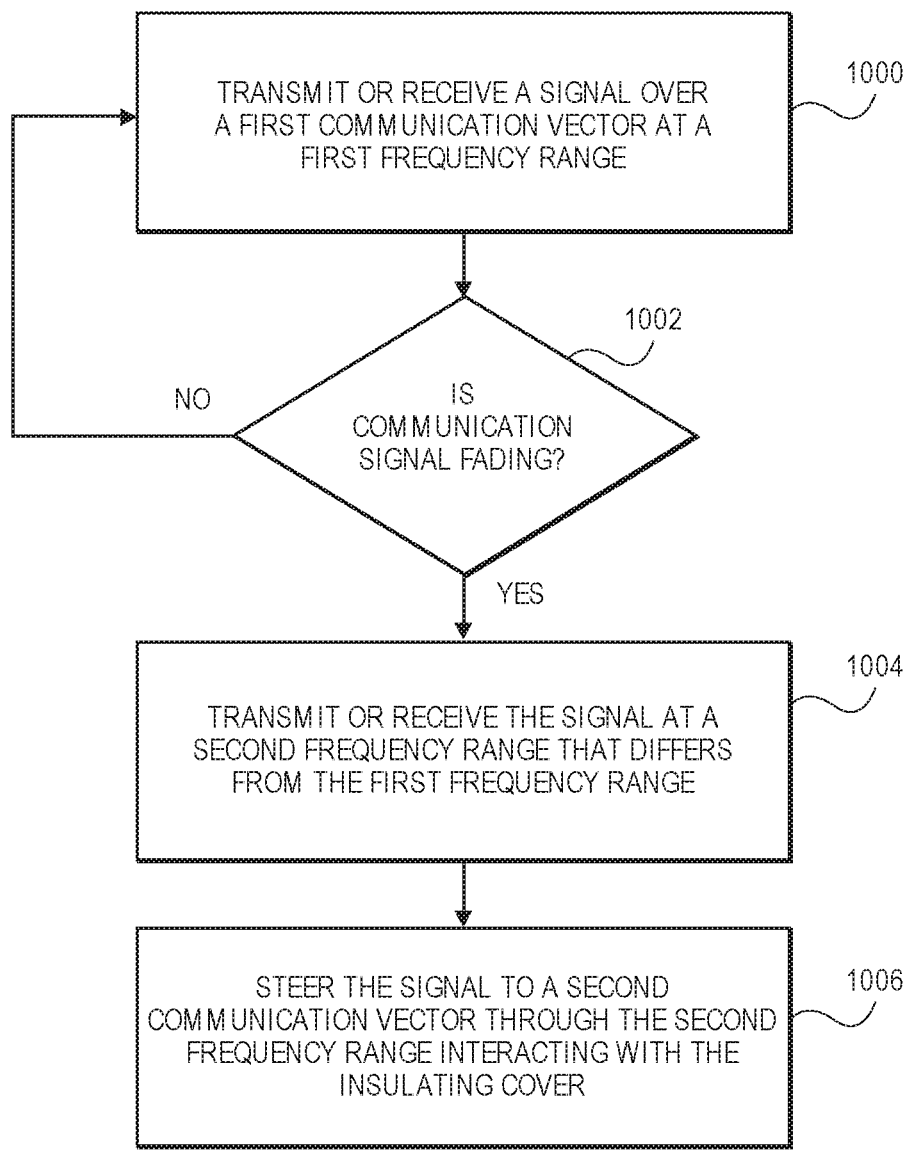
FIG. 10 illustrates a flow chart of a method of operating an IMD, according to at least one embodiment of the present disclosure.

FIG. 10 illustrates a flow chart of a method of operating an IMD, according to an embodiment of the present disclosure. At 1000, a signal, such as a communication signal, is transmitted over a first communication vector at a first frequency range. For example, an external or remote programmer may instruct the IMD to transmit or receive the signal at the first frequency range.

At 1002, it is determined if the communication signal is fading. For example, the IMD and/or the programmer may include circuitry that detects whether the signal is fading. If the communication signal is not fading, the process returns to 1000.

If, however, the communication signal is fading, the process continues to 1004, in which the communication signal is transmitted or received at a second frequency range that differs from the first frequency range. At 1006, the communication signal is steered to a second communication vector through the second frequency range interacting with an insulating cover (that defines one or more sub-electrodes) of the IMD. It may be determined whether or not the communication signal is fading. If it is, the second frequency range may be changed to a third frequency range, for example, which may then steer the communication vector away from the second communication vector.

Figure 11:
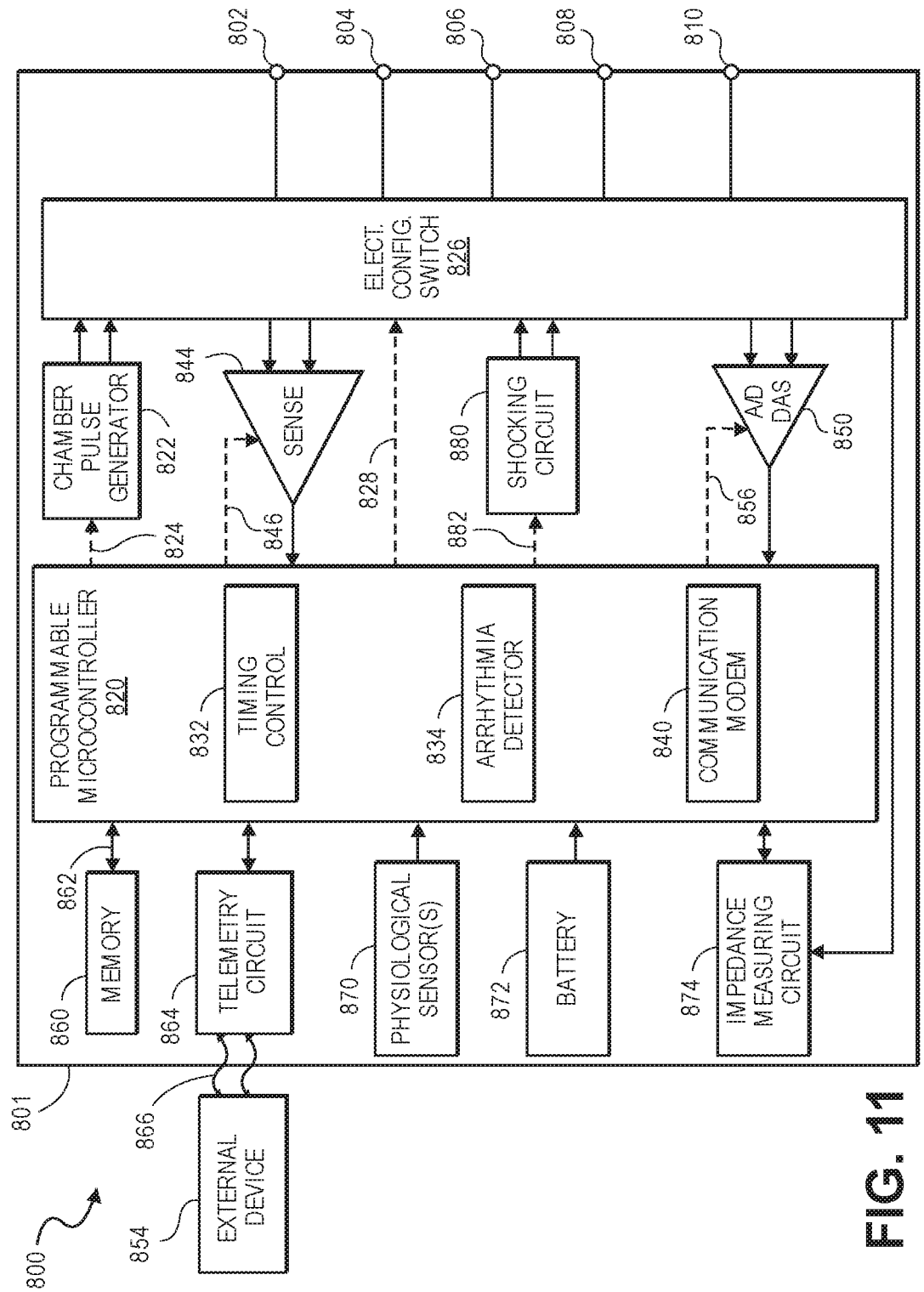
FIG. 11 illustrates a schematic block diagram showing internal components of an IMD, according to an embodiment of the present disclosure.

FIG. 11 illustrates a schematic block diagram showing internal components of an IMD 800, according to an embodiment of the present disclosure. In other embodiments, the IMD 800 may have more or fewer components than are illustrated and described in FIG. 5. In addition, in other embodiments, the IMD 800 may have a different arrangement of the components, such that some components illustrated as two discrete components may be combined into one single component or vice-versa.

The IMD 800 has a housing 801 to hold the electronic/computing components. The housing 801 (which is often referred to as the "can", "case", "encasing", or "case electrode") may be programmably selected to act as the return electrode for certain stimulus modes. Housing 801 further includes a plurality of terminals 802, 804, 806, 808, 810 that may interface with electrodes of the IMD 800. Since the IMD 800 is leadless, the terminals 802-810 may be located at or at least proximate to the electrodes, which are disposed on or extend from the housing 801.

The terminals 802-810 may be connected to an electrode configuration switch 826. The switch 826 includes multiple switches for connecting the desired electrodes or sub-electrodes to the appropriate I/O circuits, thereby facilitating electrode programmability.

The IMD 800 includes a programmable microcontroller 820 that controls various operations of the IMD 800, including cardiac monitoring and stimulation therapy. Microcontroller 820 includes a microprocessor (or equivalent control circuitry), RAM and/or ROM memory, logic and timing circuitry, state machine circuitry, and I/O circuitry. The microcontroller 820 may be or include a processor, for example. The microcontroller 820 includes the ability to process or monitor input signals (data) as controlled by a program code stored in a designated block of memory. The details of the design and operation of the microcontroller 820 are not critical to the invention, and any suitable microcontroller 820 may be used that carries out the functions described herein.

Microcontroller 820 is illustrated as including timing control circuitry 832 to control the timing of the stimulation energy or pulses (e.g., pacing rate, atrio-ventricular (AV) delay etc.). The timing control circuitry 832 may also be used for the timing of refractory periods, blanking intervals, noise detection windows, evoked response windows, alert intervals, marker channel timing, and so on. Microcontroller 820 also has an arrhythmia detector 834 for detecting arrhythmia conditions. Although not shown, the microcontroller 820 may further include other dedicated circuitry and/or firmware/software components that assist in monitoring various conditions of the patient's heart and managing pacing therapies.

The IMD 800 further includes a pulse generator 822 that generates stimulation pulses for delivery by one or more electrodes coupled thereto. The pulse generator 822 is controlled by the microcontroller 820 via control signals 824. The pulse generator 822 is coupled to the select electrode(s) via the electrode configuration switch 826. The switch 826 is controlled by control signals 828 from a microcontroller 820. Although only a single pulse generator 822 is illustrated in FIG. 5, optionally the IMD 800 may include multiple pulse generators similar to pulse generator 822, and each pulse generator may be coupled to one or more electrodes and controlled by the microcontroller 820 to deliver select stimulus pulse(s) to the corresponding one or more electrodes.

The IMD 800 includes a sensing circuit 844 selectively coupled to one or more electrodes through the switch 826. The sensing circuit 844 detects the presence of cardiac activity in certain chambers of the heart. The sensing circuit 844 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the sensing circuit 844 to sense low amplitude signals. Switch 826 determines the sensing polarity of the cardiac signal by selectively closing the appropriate switches. In this way, the clinician may program the sensing polarity independent of the stimulation polarity.

The output of the sensing circuit 844 is connected to the microcontroller 820 which, in turn, triggers or inhibits the pulse generator 822 in response to the absence or presence of cardiac activity. The sensing circuit 844 receives a control signal 846 from the microcontroller 820 for purposes of controlling the gain, threshold, polarization charge removal circuitry (not shown), and the timing of any blocking circuitry (not shown) coupled to the inputs of the sensing circuitry. Although only a single sensing circuit 844 is illustrated in FIG. 5, optionally the IMD 800 may include multiple sensing circuits, similar to sensing circuit 844. Each sensing circuit may be coupled to one or more electrodes and controlled by the microcontroller 820 to sense electrical activity detected at the corresponding one or more electrodes. The sensing circuit 844 may operate in a unipolar sensing configuration or in a bipolar sensing configuration.

The IMD 800 further includes an analog-to-digital (A/D) data acquisition system (DAS) 850 coupled to one or more electrodes via the switch 826 to sample cardiac signals across any pair of desired electrodes. The data acquisition system 850 is configured to acquire intracardiac electrogram signals, convert the raw analog data into digital data, and store the digital data for later processing and/or telemetric transmission to an external device 854 (e.g., a programmer, local transceiver, or a diagnostic system analyzer). The data acquisition system 850 is controlled by a control signal 856 from the microcontroller 820.

The microcontroller 820 is coupled to a memory 860 by a suitable data/address bus 862. The programmable operating parameters used by the microcontroller 820 are stored in memory 860 and used to customize the operation of the IMD 800 to suit the needs of a particular patient. Such operating parameters define, for example, pacing pulse amplitude, pulse duration, electrode polarity, rate, sensitivity, automatic features, arrhythmia detection criteria, and the amplitude, waveform, and vector of each shocking pulse to be delivered to the patient's heart within each respective tier of therapy.

The operating parameters of the IMD 800 may be non-invasively programmed into the memory 860 through a telemetry circuit 864 in telemetric communication via communication link 866 with the external device 854. The telemetry circuit 864 allows intracardiac electrograms and status information relating to the operation of the IMD 800 (as contained in the microcontroller 820 or memory 860) to be sent to the external device 854 through the established communication link 866.

The IMD 800 can further include magnet detection circuitry (not shown) coupled to the microcontroller 820, to detect when a magnet is placed over the device. A magnet may be used by a clinician to perform various test functions of the IMD 800 and/or to signal the microcontroller 820 that the external programmer 854 is in place to receive or transmit data to the microcontroller 820 through the telemetry circuits 864.

The IMD 800 may be equipped with a communication modem (modulator/demodulator) 840 to enable wireless communication with a remote device, such as a second implanted IMD in a master/slave arrangement, such as described in U.S. Pat. No. 7,630,767. In one implementation, the communication modem 840 uses high frequency modulation. As one example, the modem 840 transmits signals between a pair of IMD electrodes, such as between the housing 801 and anyone of the electrodes connected to terminals 802-810. The signals are transmitted in a high frequency range of approximately 20-80 kHz, as such signals travel through the body tissue in fluids without stimulating the heart or being felt by the patient. The communication modem 840 may be implemented in hardware as part of the microcontroller 820, or as software/firmware instructions programmed into and executed by the microcontroller 820. Alternatively, the modem 840 may reside separately from the microcontroller 820 as a standalone component.

The IMD 800 can further include one or more physiologic sensors 870. Such sensors are commonly referred to as "rate-responsive" sensors because they are typically used to adjust pacing stimulation rates according to the exercise state of the patient. However, the physiological sensor 870 may further be used to detect changes in cardiac output, changes in the physiological condition of the heart, or diurnal changes in activity (e.g., detecting sleep and wake states). Signals generated by the physiological sensors 870 are passed to the microcontroller 820 for analysis. The microcontroller 820 responds by adjusting the various pacing parameters (such as rate, AV Delay, V-V Delay, etc.) at which the atrial and/or ventricular pacing pulses are administered. While shown as being included within the IMD 800, the physiologic sensor(s) 870 may be external to the device 100, yet still be implanted within or carried by the patient. Examples of physiologic sensors might include sensors that, for example, sense respiration rate, pH of blood, ventricular gradient, activity, position/posture, temperature, minute ventilation, and so forth.

A battery 872 provides operating power to all of the components in the IMD 800. The battery 872 is capable of operating at low current drains for long periods of time, and is capable of providing high-current pulses (for capacitor charging) when the patient requires a shock pulse. For example, the battery 872 may be configured to provide pulses in excess of 2 amps at voltages above 2 volts for periods of 10 seconds or more. The battery 872 may also have a predictable discharge characteristic so that elective replacement time can be detected. As one example, the IMD 800 includes lithium/silver vanadium oxide batteries.

The IMD 800 further includes an impedance measuring circuit 874. The impedance measuring circuit 874 may be used for impedance surveillance during the acute and chronic phases for proper IMD 800 positioning or dislodgement. The impedance measuring circuit 874 may also be used for detecting, such as detecting operable electrodes and automatically switching to an operable pair if dislodgement occurs, detecting when the device has been implanted, and detecting the opening of heart valves. Furthermore, the impedance measuring circuit 874 may be used for measuring, such as measuring respiration or minute ventilation, measuring thoracic impedance, measuring stroke volume, and the like. The impedance measuring circuit 874 is coupled to the switch 826 so that the impedance measuring circuit 874 may use any desired electrode.

The IMD 800 may further include a shocking circuit 880, which is controlled by the microcontroller 820 by way of control signals 882. The shocking circuit 880 generates shocking pulses of low (e.g., up to 0.5 joules), moderate (e.g., 0.5-10 joules), or high energy (e.g., 10 to 40 joules), as controlled by the microcontroller 820. Such shocking pulses are applied to the patient's heart through shocking electrodes, if available on the IMD 800. It is noted that the shock therapy circuitry is optional and may not be implemented in the IMD 800, as the various embodiments described above and further below may not be configured to deliver high voltage shock pulses. On the other hand, it should be recognized that the IMD 800 may be used within a system that includes backup shock capabilities, and hence such shock therapy circuitry may be included in the IMD 800.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory, which may store the modules. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer," "control unit," "controller," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "control unit," "controller," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

The invention claimed is:

1. A method of communicating with an implantable medical device (IMD), the method comprising:
    forming a plurality of sub-electrodes on the IMD at least partially through an insulating cover, wherein at least one sub-electrode comprises a thinned area;
    adjusting a communication frequency of the IMD with a controller; and
    changing a communication vector of the IMD through interaction of the adjusting and physical properties of at least the insulating cover.

2. The method of claim 1, wherein the IMD comprises a housing, the housing comprising a single electrode, and wherein the forming comprises forming the plurality of sub-electrodes on the housing by segmenting the single electrode of the housing into the plurality of sub-electrodes.

3. The method of claim 1, further comprising configuring the insulating cover to yield controlled capacitances, wherein the controlled capacitances are a function of one or more of thicknesses, shapes, areas, or locations of segments of the insulating cover on the housing.

4. The method of claim 1, wherein the forming comprises layering different thicknesses of insulating material onto a housing of the IMD.

5. The method of claim 1, further comprising positioning a conductive metal in the thinned area of the at least one sub-electrode.

6. The method of claim 1, further comprising coupling a tip electrode to a housing of the IMD, wherein changing the communication vector of the IMD comprises changing the communication vector of the IMD through interaction of the adjusting and physical properties of the insulating cover and physical properties of the electrode tip.

7. The method of claim 6, further comprising splitting the tip electrode into tip sub-electrodes.

8. The method of claim 1, further comprising transmitting and receiving communication signals through the plurality of sub-electrodes at different spatial orientations and different relative phase shifts.

9. The method of claim 1, wherein the plurality of sub-electrodes are configured to transmit and receive signals at different spatial orientations and at different relative phase shifts.

10. The method of claim 1, further comprising transmitting a communication signal, wherein the plurality of sub-electrodes comprise a first and a second sub-electrodes, wherein the first and second sub-electrodes introduce a first and second phase shift into the communication signal.

11. A method of communicating with an implantable medical device (IMD), the method comprising:
    forming a plurality of sub-electrodes on the IMD at least partially through an insulating cover or an absence thereof, wherein the plurality of sub-electrodes comprise at least one thinned area;
    transmitting or receiving a first communication signal over a first communication vector at a first frequency range;
    determining that the first communication signal is fading;
    transmitting or receiving a second communication signal at a second frequency range, wherein the first frequency range differs from the second frequency range; and
    steering the communication signal to a second communication vector through the second frequency range interacting with at least the insulating cover.

12. The method of claim 11, wherein forming comprises layering different thicknesses of insulating material onto a housing of the IMD.

13. The method of claim 11, further comprising positioning a conductive metal in the at least one thinned area.

14. The method of claim 11, further comprising coupling a tip electrode to a housing of the IMD, wherein steering comprises steering the communication signal to a second communication vector through the second frequency range interacting with the insulating cover and the electrode tip.

15. The method of claim 14, further comprising splitting the tip electrode into tip sub-electrodes.

16. The method of claim 11, wherein steering the communication signal to a second communication vector through the second frequency range interacting with at least the insulating cover comprises transmitting and/or receiving communication signals through the plurality of sub-electrodes at different spatial orientations and/or different relative phase shifts.

* * * * *